United States Patent [19]

Fanslow et al.

[11] Patent Number: 5,223,605
[45] Date of Patent: Jun. 29, 1993

[54] INTERLEUKIN-4 BINDING PROTEIN-γ

[75] Inventors: William C. Fanslow, Federal Way; Richard J. Armitage, Seattle, both of Wash.

[73] Assignee: Immunex Corporation, Seattle, Wash.

[21] Appl. No.: 598,489

[22] Filed: Oct. 16, 1990

Related U.S. Application Data

[63] Continuation-in-part of Ser. No. 509,672, Apr. 16, 1990, abandoned.

[51] Int. Cl.$^5$ .............................................. C07K 15/00
[52] U.S. Cl. .................................. 530/350; 530/351; 530/395; 530/827; 530/389.1; 930/141; 435/69.1; 435/69.52
[58] Field of Search ............... 530/350, 351, 395, 387; 435/69.1, 69.52; 930/141

[56] References Cited

FOREIGN PATENT DOCUMENTS 8909621 10/1989 PCT Int'l Appl. .

OTHER PUBLICATIONS

Solari et al, *Biochem J.* 262, 1989, pp. 897-908.
Ogata et al *DNAS* 86, 1989, pp. 4215-4219.
Larche et al *Immunology* 65, 1988, pp. 617-622.
Ohara et al, *Nature* 315, 1985, pp. 333-336.
Foxwell et al *Eur J. Immunol.* 19, 1989, pp. 1637-1641.
Harada et al, CA vol. 111, 1989, #230163x.
Harada et al., *Expression cloning of a cDNA encoding the murine interleukin 4 receptor based on ligand binding,* Proc. Nat. Acad Sci. 87:857 (1990).
"Purification of a 130-kDa T Cell Glycoprotein That Binds Human Interleukin 4 with High Affinity", *The Journal of Biological Chemistry,* vol. 265, pp. 439-444.
"The Murine Interleukin-4 Receptor: Molecular Cloning and Characterization of Secreted and Membrane Bound Forms", *Cell,* vol. 59, pp. 335-348.
"Human Interleukin-4 Receptor Confers Biological Respionsiveness and Defines a Novel Receptor Superfamily", Rejean L. Idzerda, et al., *J. Exp. Med.,* vol. 171, Mar. 1990, pp. 861-873.

*Primary Examiner*—Garnette D. Draper
*Attorney, Agent, or Firm*—Patricia Anne Perkins; Christopher L. Wight; Scott G. Hallquist

[57] ABSTRACT

Isolated and purified Interleukin-4 Binding Protein-γ (IL-4bpγ) and methods for obtaining isolated and purified IL-4bpγ.

4 Claims, 1 Drawing Sheet

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: N ( v ) FRAGMENT TYPE: N-terminal
    ( v i ) ORIGINAL SOURCE:
        ( A ) ORGANISM: Homo sapiens
        ( G ) CELL TYPE: B-cell precursor
        ( H ) CELL LINE: JM-1

( x i ) SEQUENCE DESCRIPTION: SEQ ID NO:1:

```
Thr Ser Pro Gln Gln Pro Ala Ala Arg Pro Ser Asp Leu Leu Ser Leu
1               5                   10                  15

Asp Gly Ser
```

INTERLEUKIN-4 BINDING PROTEIN-γ

CROSS-REFERENCE TO RELATED APPLICATION

This application is a continuation-in-part of application Ser. No. 509,672, filed Apr. 16, 1990, now abandoned.

BACKGROUND OF THE INVENTION

The present invention relates generally to proteins which bind Interleukin-4 and, more specifically, to compositions containing isolated Interleukin-4 binding proteins.

Interleukin-4 (IL-4) is one of many cytokines which regulate the function of immune cells. IL-4 has broad effects on B cells, such as enhancing the secretion of IgE and IgG₁ isotypes in activated B cells. In addition, IL-4 promotes the proliferation and differentiation of T lymphocytes, as well as a wide range of hematopoietic cell lineages. IL-4 mediates its effects by binding to cell surface receptors and initiating a complex series of events within the responsive cell. Cloning of the murine and human IL-4 receptors have recently been reported by Mosley et al., *Cell* 59:335 (1989) and Idzerda et al., *J. Exp. Med.* 171:861 (1990).

The immune system can malfunction, resulting in autoimmune diseases such as arthritis, diabetes, allergy and asthma. In some instances normal immune responses are also undesirable, such as when the immune system attacks and causes rejection of transplanted organs. IL-4 has been shown to play a specific role in activating immune cells to produce antibodies responsible for allergic and asthmatic reactions, and to attack transplanted tissue. Mosely et al. (supra) identified naturally occurring soluble forms of the IL-4 receptor consisting of the extracellular region of the receptor and which function as IL-4 antagonists by binding to IL-4, thus preventing IL-4 from binding to a cell surface receptor and transducing an IL-4 biological signal. Such IL-4 antagonists may be of clinical use in inhibiting IL-4 mediated immune responses, for example in alleviating or preventing IgE-induced allergic responses or rejection of transplanted tissue.

A specie of IL-4 antagonist has recently been isolated from human urine using an IL-4 affinity column. This IL-4 antagonist, designated IL-4 binding protein-β or IL-4bpβ, is unique, having an N-terminal amino acid sequence distinct from human or murine IL-4 receptor. IL-4bpβ is described in detail in copending U.S. patent application Ser. No. 07/667,687, filed Mar. 8, 1991.

The present invention provides yet another distinct specie of IL-4 antagonist which is referred to as Interleukin-4 Binding Protein-γ, or IL-4bpγ. The N-terminal amino acid sequence of IL-4bpγ indicates that this protein is distinct from IL-4bpβ and from murine and human IL-4 receptors.

SUMMARY OF THE INVENTION

The present invention provides an isolated mammalian IL-4 binding protein, referred to herein as IL-4bpγ. Specifically, the present invention provides isolated human IL-4bpγ. IL-4bpγ of the present invention is capable of inhibiting IL-4 binding to IL-4 receptor molecules.

IL-4bpγ is a glycoprotein which is isolable from human JM-1 cells, has an apparent molecular weight of about 45-50 kilodaltons (kDa) by SDA-PAGE and an N-terminal amino acid sequence of ThrSerProGlnGln-ProAlaAlaArgProSerAspLeuLeuSerLeuAspGlySer. This sequence indicates that the IL-4bpγ disclosed herein is distinct from murine and human IL-4 receptors and from IL-4bpβ, known to the art.

The present invention also provides compositions for use in therapy, diagnosis, assay of IL-4bpγ, IL-4 or IL-4 receptors, or in raising antibodies to IL-4bpγ, comprising effective quantities of IL-4bpγ prepared according to the foregoing processes.

The identification and purification of IL-4bpγ enables study of its structure and biological characteristics and the role it plays in the responses of various cell populations to IL-4 or other cytokine stimulation.

These and other aspects of the present invention will become evident upon reference to the following brief description of the drawings and detailed description.

BRIEF DESCRIPTION OF THE SEQUENCE LISTING

SEQUENCE ID No. 1 is a partial N-terminal amino acid sequence of the IL-4bpγ of the present invention.

DETAILED DESCRIPTION OF THE INVENTION

Definitions

Figure 1:
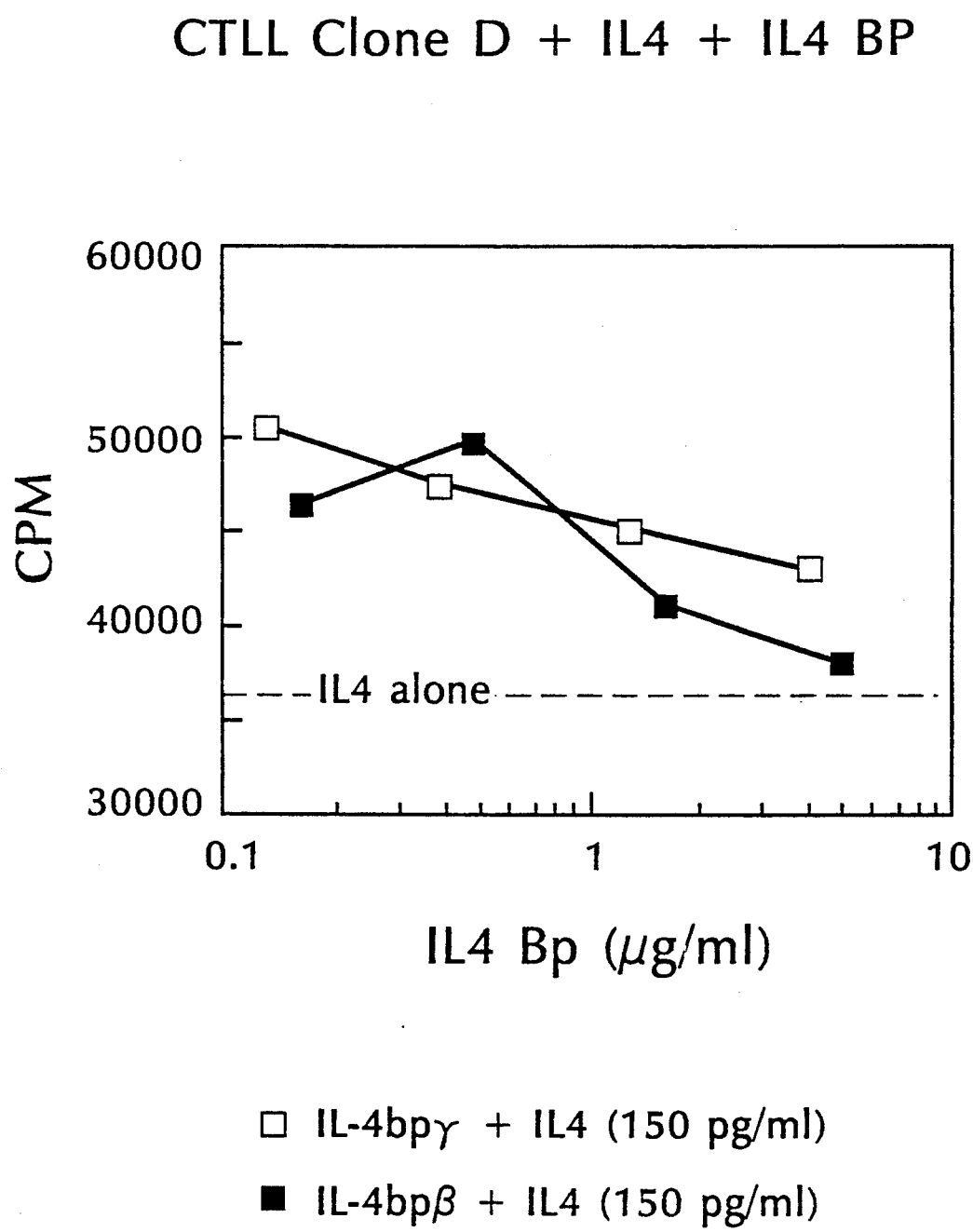
FIG. 1 is a graph showing that increasing concentrations of IL-4bpβ (■) and IL-4bpγ (-□-) inhibit IL-4 dependent proliferation of CTLL cells transfected with human IL-4 receptor in a dose-dependent fashion.

As used herein, the terms "IL-4 Binding Protein-γ" and "IL-4bpγ" refer to proteins which are capable of binding to IL-4 and are isolable, for example, from human JM-1 cells. IL-4bpγ also has an apparent molecular weight of about 45-50 kDa by SDS-PAGE (depending on the degree of glycosylation) and an N-terminal amino acid sequence of ThrSerProGlnGln-ProAlaAlaArgProSerAspLeuLeuSerLeuAspGlySer (Sequence ID No. 1). The term IL-4bpγ includes, but is not limited to, analogs or subunits of IL-4bpγ which are substantially similar to human IL-4bpγ and which exhibit at least some biological activity in common with IL-4bpγ. Various bioequivalent protein and amino acid analogs are described in detail below.

The term "substantially similar," when used to define either amino acid or nucleic acid sequences, means that a particular subject sequence, for example, a mutant sequence, varies from a reference sequence by one or more substitutions, deletions, or additions, the net effect of which does not ablate the IL-4 binding activity of IL-4bpγ. Substantially similar analog proteins will be greater than about 30 percent similar to the corresponding sequence of the human IL-4bpγ. Sequences having lesser degrees of similarity but comparable biological activity are considered to be equivalents. More preferably, the analog proteins will be greater than about 80 percent similar to the corresponding sequence of human IL-4bpγ, in which case they are defined as being "substantially identical." In defining nucleic acid sequences, all subject nucleic acid sequences capable of encoding substantially similar amino acid sequences are considered substantially similar to a reference nucleic acid sequence. Percent similarity may be determined, for example, by comparing sequence information using the GAP computer program, version 6.0, available from the University of Wisconsin Genetics Computer Group (UWGCG). The GAP program utilizes the alignment method of Needleman and Wunsch (*J. Mol. Biol.* 48:443, 1970), as revised by Smith and Waterman (*Adv. Appl. Math.* 2:482, 1981). Briefly, the GAP program defines similarity as the number of aligned symbols (i.e., nucleotides or amino acids) which are similar, divided by the total number of symbols in the shorter of the two sequences. The preferred default parameters for the GAP program include: (1) a unary comparison matrix (containing a value of 1 for identities and 0 for non-identities) for necleotides, and the weighted comparison matrix of Gribskov and Burgess, *Nucl. Acids Res.* 14:6745, 1986, as described by Schwartz and Dayhoff, ed., *Atlas of Protein Sequence and Structure*, National Biomedical Research Foundation, pp. 353-358, 1979; (2) a penalty of 3.0 for each gap and an additional 0.10 penalty for each symbol in each gap; and (3) no penalty for end gaps.

"Recombinant," as used herein, means that a protein is derived from recombinant (e.g., microbial or mammalian) expression systems. "Microbial" refers to recombinant proteins made in bacterial or fungal (e.g., yeast) expression systems. As a product, "recombinant microbial" defines a protein produced in a microbial expression system which is essentially free of native endogenous substances. Protein expressed in most bacterial cultures, e.g., *E. coli*, will be free of glycan. Protein expressed in yeast may have a glycosylation pattern different from that expressed in mammalian cells.

"Biologically active," as used throughout the specification as a characteristic of IL-4bpγ, means that a particular molecule is capable of binding detectable quantities of IL-4 or inhibiting IL-4 from binding to membrane bound IL-4 receptor molecules and transducing an IL-4 signal.

"Isolated and purified", as used in the context of the present invention to define the purity of proteins, refers to human IL-4bpγ which is substantially free of other human proteins of natural or endogenous origin and contains less than about 1% by mass of protein contaminants residual of production processes. Such compositions, however, can contain other proteins added as stabilizers, carriers, excipients or co-therapeutics. Isolated and purified IL-4pbγ is detectable as a single protein band in a polyacrylamide gel by silver staining.

Isolation of IL-4bpγ From Cell Supernatants

IL-4bpγ can be isolated from supernatants of the JM-1 cell line. JM-1 was obtained as a spontaneous cell line from peripheral blood of a patient with an immunoblastic B cell lymphoma-leukemia and was positive for HLA-Dr (91%), CD19 (76%), and CD10 (91%), negative for surface μ, CD7, My7, and My9, and marginally TdT positive. The JM-1 cell line was obtained from Dr. Jack Singer, Veterans Administration Medical Center, Seattle, Wash. 98108 and was deposited on Apr. 17, 1990 with the American Type Culture Collection, 12301 Parklawn Drive, Rockville, Md. 20852, USA, under accession number 10423.

It is expected that other pre-B cell lines, such a BMB or Nalm-6, may also be used as a source of IL-4bpγ. BMB is a cell line which was obtained from a patient with an early B cell lineage tumor and was positive for HLA-Dr (100%), CD19 (100%), CD10 (62%), CD20 (99%), CD24 (46%), CD38 (74%), and surface μ (50%) and negative for CD3, CD4, CD8, CD16, and Mac-1.

Nalm-6 is a cell line which has been previously described by Hurwitz, et al., *Int. J. Cancer* 23:174 (1979).

In a preferred aspect of the present invention, IL-4pbγ is isolated from supernatants of the JM-1 cell line. For example, JM-1 cells are grown to high density and conditioned media from the cells in concentrated 200-400 fold using a commercially available protein concentration filter, for example, an Amicon Centriprep-10® or Millipore Pellicon ultrafiltration unit. Cellular debris is preferably removed from the retentate by filtering on 0.22μ filters. The concentrate is then applied to a suitable purification matrix that is capable of purifying protein from a complex solution. In the preferred aspects of IL-4bpγ purification, the purification matrix comprises IL-4 molecules bound to a suitable support. Alternatively, the purification matrix comprises an anti-IL-4bpγ antibody molecule bound to a suitable support. The matrix to which the IL-4 or antibody is bound can be acrylamide, agarose, dextran, cellulose or other types commonly employed in protein purification.

Optionally, one or more reversed-phase high performance liquid chromatography (RP-HPLC) steps employing hydrophobic RP-HPLC media, e.g., silica gel having pendant methyl or other aliphatic groups, can be employed to further purify an IL-4bpγ composition. Some or all of the foregoing purification steps, in various combinations, can also be employed to provide a homogeneous recombinant protein.

Proteins and Analogs

The present invention provides isolated recombinant mammalian IL-4bpγ proteins. Such proteins are substantially free of contaminating endogenous materials. Human IL-4bpγ is isolated from human JM-1 cells as a glycoprotein having an apparent molecular weight by SDS-PAGE of about 45-50 kDa. Derivatives of IL-4bpγ within the scope of the invention also include various structural forms of the primary protein which retain biological activity, for example, non-glycosylated forms produced by expression of recombinant DNAs in transformed prokaryotic cells. Due to the presence of ionizable amino and carboxyl groups, for example, an IL-4bpγ protein may be in the form of acidic or basic salts, or in neutral form. Individual amino acid residues may also be modified by oxidation or reduction.

The primary amino acid structure may be modified by forming covalent or aggregative conjugates with other chemical moieties, such as glycosyl groups, lipids, phosphate, acetyl groups and the like, or by creating amino acid sequence mutants. Covalent derivatives are prepared by linking particular functional groups to IL-4bpγ amino acid side chains or at the N- or C-Termini. Other derivatives of IL-4bpγ within the scope of this invention include covalent or aggregative conjugates of IL-4bpγ or its fragments with other proteins or polypeptides, such as by synthesis in recombinant culture as N-terminal or C-terminal fusions. For example, the conjugated peptide may be a signal (or leader) polypeptide sequence at the N-terminal region of the protein which co-translationally or post-translationally directs transfer of the protein from its site of synthesis to its site of function inside or outside of the cell membrane or wall (e.g., the yeast α-factor leader). IL-4bpγ protein fusions can comprise peptides added to facilitate purification or identification of IL-4bpγ (e.g., poly-His). The amino acid sequence of IL-4bpγ can also be linked to the peptide Asp-Tyr-Lys-Asp-Asp-Asp-Asp-Lys (DYKDDDDK) (Hopp et al., *Bio/Technology* 6:1204, 1988.) The latter sequence is highly antigenic and provides an epitope reversibly bound by a specific monoclonal antibody, enabling rapid assay and facile purification of expressed recombinant protein. This sequence is also specifically cleaved by bovine mucosal enterokinase at the residue immediately following the Asp-Lys paring. Fusion proteins capped with this peptide may also be resistant to intracellular degradation in *E. coli*.

IL-4bpγ derivatives may also be used as immunogens, reagents in immunoassays, or as binding agents for affinity purification procedures of IL-4 or other binding ligands. IL-4bpγ derivatives may also be obtained by cross-linking agents, such as M-maleimidobenzoyl succinimide ester and N-hydroxysuccinimide, at cysteine and lysine residues. IL-4bpγ proteins may also be covalently bound through reactive side groups to various insoluble substrates, such as cyanogen bromide-activated, bisoxirane-activated, carbonyldiimidazole-activated or tosyl-activated agarose structures, or by adsorbing polyolefin surfaces (with or without glutaraldehyde cross-linking). Once bound to a substrate, IL-4bpγ may be used to selectively bind (for purposes of assay or purification) anti-IL-4bpγ antibodies or IL-4.

The present invention also includes IL-4bpγ with or without associated native-pattern glycosylation. Recombinant IL-4bpγ expressed in yeast or mammalian expression systems, e.g., COS-7 cells, may be similar or significantly different in molecular weight and glycosylation pattern than the native molecules, depending upon the expression system. Expression of IL-4bpγ DNAs in bacteria such as *E. coli* provides nonglycosylated molecules. Functional mutant analogs of mammalian IL-4bpγ having inactivated N-glycosylation sites can be produced by oligonucleotide synthesis and ligation or by site-specific mutagenesis techniques. These analog proteins can be produced in a homogeneous, reduced-carbohydrate form in good yield using yeast expression systems. N-glycosylation sites in eukaryotic proteins are characterized by the amino acid triplet Asn-$A_1$-Z, where $A_1$ is any amino acid except Pro, and Z is Ser or Thr. In this sequence, asparagine provides a side chain amino group for covalent attachment of carbohydrate. Such a site can be eliminated by substituting another amino acid for Asn or for residue Z, deleting Asn or Z, or inserting a non-Z amino acid between $A_1$ and Z, or an amino acid other than Asn between Asn and $A_1$.

IL-4bpγ derivatives may also be obtained by mutations of IL-4bpγ. An IL-4bpγ mutant, as referred to herein, is a polypeptide homologous to IL-4bpγ but which has an amino acid sequence different from native IL-4bpγ because of a deletion, insertion or substitution. Like most mammalian genes, mammalian IL-4bpγ is presumably encoded by multi-exon genes. Alternative mRNA constructs which can be attributed to different mRNA splicing events following transcription, and which share large regions of identity or similarity with the cDNAs claimed herein, are considered to be within the scope of the present invention.

Bioequivalent analogs of IL-4bpγ proteins may be constructed by, for example, making various substitutions of residues or sequences or deleting terminal or internal residues or sequences not needed for biological activity. For example, cysteine residues can be deleted or replaced with other amino acids to prevent formation of incorrect intramolecular disulfide bridges upon renaturation. Other approaches to mutagenesis involve modification of adjacent dibasic amino acid residues to enhance expression in yeast systems in which KEX2 protease activity is present. Generally, substitutions should be made conservatively; i.e., the most preferred substitute amino acids are those having physicochemical characteristics resembling those of the residue to be replaced. Similarly, when a deletion or insertion strategy is adopted, the potential effect of the deletion or insertion on biological activity should be considered.

Subunits of IL-4bpγ may be constructed by deleting terminal or internal residues or sequences. The resulting protein is an IL-4bpγ molecule which retains its ability to bind IL-4.

Mutations in nucleotide sequences constructed for expression of analog IL-4bpγ must, of course, preserve the reading frame phase of the coding sequences and preferably will not create complementary regions that could hybridize to produce secondary mRNA structures, such as loops or hairpins, which would adversely affect translation of the IL-4bpγ mRNA. Although a mutation site may be predetermined, it is not necessary that the nature of the mutation per se be predetermined. For example, in order to select for optimum characteristics of mutants at a given site, random mutagenesis may be conducted at the target codon and the expressed IL-4bpγ mutants screened for the desired activity.

Not all mutations in the nucleotide sequence which encodes IL-4bpγ will be expressed in the final product, for example, nucleotide substitutions may be made to enhance expression, primarily to avoid secondary structure loops in the transcribed mRNA (see EPA 75,444A, incorporated herein by reference), or to provide codons that are more readily translated by the selected host, e.g., the well-known *E. coli* preference codons for *E. coli* expression.

Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene having particular codons altered according to the substitution, deletion, or insertion required. Exemplary methods of making the alterations set forth above are disclosed by Walder et al. (*Gene* 42:133, 1986); Bauer et al. (*Gene* 37:73, 1985); Craik (*BioTechniques*, January 1985, 12-19); Smith et al. (*Genetic Engineering: Principles and Methods*, Plenum Press 1981); and U.S. Pat. Nos. 4,518,584 and 4,737,462, which are incorporated by reference herein.

Expression of Recombinant IL-4bpγ

Isolated human IL-4bpγ may also be produced by recombinant DNA techniques. Briefly, a recombinant DNA clone encoding IL-4bpγ is isolated and inserted into an appropriate expression vector, which is then integrated into a host microorganism. The host microorganism expresses the recombinant IL-4bpγ protein and the protein is purified from cell extracts or cell supernatants.

Recombinant production of genes first requires the isolation of a recombinant DNA clone encoding a particular gene or mRNA sequence. Such recombinant DNA clones are isolated from primary cells or cell lines which constitutively express IL-4bpγ, such as the JM-1 cell line. The isolated DNA is preferably in the form of an open reading frame uninterrupted by internal non-translated sequences, or introns. Genomic DNA containing the relevant sequences can also be used. Such isolated DNA fragments are inserted into a recombinant expression vector to amplify or express the DNA which encodes the desired protein.

Recombinant expression vectors include synthetic or cDNA-derived DNA fragments encoding human IL-4bpγ or bioequivalent analogs operably linked to suitable transcriptional or translational regulatory or structural elements derived from mammalian, microbial, viral or insect genes. Such regulatory elements include a genetic element or elements having a regulatory role in gene expression, for example, transcriptional promoters or enhancers, an optional operator sequence to control transcription, a sequence encoding suitable mRNA ribosomal binding sites, and appropriate sequences which control transcription and translation initiation and termination, as described in detail below. The ability to replicate in a host, usually conferred by an origin of replication, and a selection gene to facilitate recognition of transformants may additionally be incorporated. Structural elements intended for use in yeast expression systems preferably include a leader sequence enabling extracellular secretion of translated protein by a host cell. Alternatively, where recombinant protein is expressed without a leader to transport sequence, it may include an N-terminal methionine residue. This residue may optionally be subsequently cleaved from the expressed recombinant protein to provide a final product. DNA regions are operably linked when they are functionally related to each other. For example, DNA for a signal peptide (secretory leader) is operably linked to DNA for a polypeptide if it is expressed as a precursor which participates in the secretion of the polypeptide; a promoter is operably linked to a coding sequence if it controls the transcription of the sequence; or a ribosome binding site is operably linked to a coding sequence if it is positioned so as to permit translation. Generally, operably linked means contiguous and, in the case of secretory leaders, contiguous and in reading frame.

DNA sequences encoding human IL-4bpγ which are to be expressed in a microorganism will preferably contain no introns that could prematurely terminate transcription of DNA into mRNA; however, premature termination of transcription may be desirable, for example, where it would result in mutants having advantageous C-terminal truncations, for example, deletion of nuecloetides which encode amino acids not necessary for biological activity or binding activity. Due to code degeneracy, there can be considerable variation in nucleotide sequences encoding the same amino acid sequence.

The recombinant expression vectors carrying the recombinant IL-4bpγ insert are then transformed into a substantially homogeneous monoculture of suitable host microorganisms, for example, bacteria such as E. coli, yeast such as S. cerevisiae, or a mamalian cell line such as Chinese Hamster Ovary (CHO) cells, which stably integrate the vector/insert into chromosomal DNA or carry the recombinant transcriptional unit as a component of a resident plasmid. Generally, cells constituting the system are the progeny of a single ancestral transformant. Recombinant expression systems most preferably express heterologous protein upon induction of the regulatory elements linked to the DNA sequence or synthetic gene to be expressed.

Transformed host cells are cells which have been transformed or transfected with IL-4bpγ vectors constructed using recombinant DNA techniques. Transformed host cells ordinarily express IL-4bpγ, but host cells transformed for purposes of cloning or amplifying IL-4bpγ DNA do not need to express IL-4bpγ. Expressed IL-4bpγ will be deposited in the cell membrane or secreted into the culture supernatant, depending of the IL-4bpγ DNA selected. Suitable host cells for expression of mammalian IL-4bpγ include prokaryotes, yeast or higher eukaryotic cells under the control of appropriate promoters. Prokaryotes include gram negative or gram positive organisms, for example E. coli or bacilli. Higher eukaryotic cells include established cell lines of mammalian origin as described below. Cell-free translation systems could also be employed to produce mammalian IL-4bpγ using RNAs derived from the DNA constructs of the present invention. Appropriate cloning and expression vectors for use with bacterial, fungal, yeast, and mammalian cellular hosts are described by Pouwels et al. (Cloning Vectors: A Laboratory Manual, Elsevier, N.Y., 1985), the relevant disclosure of which is hereby incorporated by reference.

Prokaryotic expression hosts may be used for expression of IL-4bpγ that do not require extensive proteolytic and disulfide processing. Prokaryotic expression vectors generally comprise one or more phenotypic selectable markers, for example a gene encoding proteins conferring antibiotic resistance or supplying an autotrophic requirement, and an origin of replication recognized by the host to ensure amplification within the host. Suitable prokaryotic hosts for transformation include E. coli, Bacillus subtilis, Salmonella typhimurium, and various species within the genera Pseudomonas, Streptomyces, and Staphylococcus, although others may also be employed as a matter of choice.

Useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega Biotec, Madison, Wis., USA). These pBR322 "backbone" sections are combined with an appropriate promoter and the structural sequence to be expressed. E. coli is typically transformed using derivatives of pBR322, a plasmid derived from an E. coli species (Bolivar et al., Gene 2:95, 1977). pBR322 contains genes for ampicillin and tetracycline resistance and thus provides simple means for identifying transformed cells.

Promoters commonly used in recombinant microbial expression vectors include the β-lactamase (penicillinase) and lactose promoter system (Chang et al., Nature 275:615, 1978; and Goeddel et al., Nature 281:544, 1979), the tryptophan (trp) promoter system (Goeddel et al., Nucl. Acids Res. 8:4057, 1980; and EPA 36,776) and tac promoter (Maniatis, Molecular Cloning: A Laboratory Manual, Cold Spring Harbor Laboratory, p. 412, 1982). A particularly useful bacterial expression system employs the phage λ $P_L$ promoter and cI857ts thermolabile repressor. Plasmid vectors available from the American Type Culture Collection which incorporate derivatives of the λ $P_L$ promotor include plasmid pHUB2, resident in E. coli strain JMB9 (ATCC 37092) and pPLc28, resident in E. coli RR1 (ATCC 53082).

Recombinant IL-4bpγ proteins may also be expressed in yeast hosts, preferably from the Saccharomyces genus, such as *S. cerevisiae*. Yeast of other genera, such as Pichia or Kluyveromyces may also be employed. Yeast vectors will generally contain an origin of replication from the 2μ yeast plasmid or an autonomously replicating sequence (ARS), promoter, DNA encoding IL-4bpγ, sequences for polyadenylation and transcription termination and a selection gene. Preferably, yeast vectors will include an origin of replication and selectable marker permitting transformation of both yeast and *E. coli*, e.g., the ampicillin resistance gene of *E. coli* and *S. cerevisiae* trp1 gene, which provides a selection marker for a mutant strain of yeast lacking the ability to grow in tryptophan, and a promoter derived from a highly expressed yeast gene to induce transcription of a structural sequence downstream. The presence of the trp1 lesion in the yeast host cell genome then provides an effective environment for detecting transformation by growth in the absence of tryptophan.

Suitable promoter sequences in yeast vectors include the promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in Hitzeman, EPA 73,657.

Preferred yeast vectors can be assembled using DNA sequences from pBR322 for selection and replication in *E. coli* (Amp$^r$ gene and origin of replication) and yeast DNA sequences including a glucose-repressible ADH2 promoter and α-factor secretion leader. The ADH2 promoter has been described by Russel et al. (*J. Biol. Chem.* 258:2674, 1982) and Beier et al. (*Nature* 300:724, 1982). The yeast α-factor leader, which directs secretion of heterologous proteins, can be inserted between the promoter and the structural gene to be expressed. See, e.g., Kurjan et al., *Cell* 30:933, 1982; and Bitter et al., *Proc. Natl. Acad. Sci. USA* 81:5330, 1984. The leader sequence may be modified to contain, near its 3' end, one or more useful restriction sites to facilitate fusion of the leader sequence to foreign genes.

Suitable yeast transformation protocols are known to those of skill in the art; an exemplary technique is described by Hinnen et al., *Proc. Natl. Acad. Sci. USA* 75:1929, 1978, selecting for Trp$^+$ transformants in a selective medium consisting of 0.67% yeast nitrogen base, 0.5% casamino acids, 2% glucose, 10 μg/ml adenine and 20 μg/ml uracil.

Host strains transformed by vectors comprising the ADH2 promoter may be grown for expression in a rich medium consisting of 1% yeast extract, 2% peptone, and 1% glucose supplemented with 80 μg/ml adenine and 80 μg/ml uracil. Derepression of the ADH2 promoter occurs upon exhaustion of medium glucose. Crude yeast supernatants are harvested by filtration and held at 4° C. prior to further purification.

Various mammalian or insect cell culture systems can be employed to express recombinant protein. Baculovirus systems for production of heterologous proteins in insect cells are reviewed by Luckow and Summers (*Bio/Technology* 6:47, 1988). Examples of suitable mammalian host cell lines include the COS-7 lines of monkey kidney cells, described by Gluzman (*Cell* 23:175, 1981), and other cell lines capable of expressing an appropriate vector including, for example, L cells, C127, 3T3, Chinese hamster ovary (CHO), HeLa and BHK cell lines. Mammalian expression vectors may comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences.

The transcriptional and translational control sequences in expression vectors to be used in transforming vertebrate cells may be provided by viral sources. For example, commonly used promoters and enhancers are derived from Polyoma, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a heterologous DNA sequence. The early and late promoters are particularly useful because both are obtained easily from the virus as a fragment which also contains the SV40 viral origin of replication (Fiers et al., *Nature* 273:113, 1978). Smaller or larger SV40 fragments may also be used, provided the approximately 250 bp sequence extending from the Hind III site toward Bgl I site located in the viral origin of replication is included. Further, mammalian genomic IL-4bpγ promoter, control and/or signal sequences may be utilized, provided such control sequences are compatible with the host cell chosen. Exemplary vectors can be constructed as disclosed by Okayama and Berg (*Mol. Cell. Biol.* 3:280, 1983).

A useful system for stable high level expression of mammalian receptor cDNAs in C127 murine mammary epithelial cells can be constructed substantially as described by Cosman et al. (*Mol. Immunol.* 23:935, 1986).

A particularly preferred eukaryotic vector for expression of IL-4bpγ DNA is pDC302 and is described by Mosley, et al. (*Cell* 59:335, 1989). pDC302 was derived from the mammalian high expression vector pDC201 and contains regulatory sequences from SV40, adenovirus-2, and human cytomegalovirus. A sample of pDC302 has been deposited with the American Type Culture Collection (ATCC) under the name pCAV/NOT-IL-7R, deposit accession number 68014.

Purification of Recombinant Human IL-4bpγ

Purified mammalian IL-4 receptors or analogs are prepared by culturing suitable host/vector systems to express the recombinant translation products of the DNAs of the present invention, which are then purified from culture media or cell extracts as described above.

For example, supernatants from systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. For example, a suitable affinity matrix can comprise an IL-4 or lectin or antibody molecule bound to a suitable support. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred.

Finally, one or more reversed-phase high performance liquid chromatography (RP-HPLC) steps employing hydrophobic RP-HPLC media, e.g., silica gel having pendant methyl or other aliphatic groups, can be employed to further purify IL-4bpγ. Some of all of the foregoing purification steps, in various combinations, can also be employed to provide an isolated recombinant protein.

Recombinant protein produced in bacterial culture is usually isolated by initial extraction from cell pellets, followed by one or more concentration, salting-out, aqueous ion exchange or size exclusion chromatography steps. Finally, high performance liquid chromatography (HPLC) can be employed for final purification steps. Microbial cells employed in expression of recombinant mammalian IL-4bpγ can be disrupted by any convenient method, including freeze-thaw cycling, sonication, mechanical disruption, or use of cell lysing agents.

Fermentation of yeast which express mammalian IL-4bpγ as a secreted protein greatly simplifies purification. Secreted recombinant protein resulting from a large-scale fermentation can be purified by methods analogous to those disclosed by Urdal et al. (*J. Chromatog.* 296:171, 1984). This reference describes two sequential, reversed-phase HPLC steps for purification of recombinant human IL-2 on a preparative HPLC column.

Human IL-4bpγ synthesized in recombinant culture is characterized by the presence of non-human cell components, including proteins, in amounts and of a character which depend upon the purification steps taken to recover human IL-4bpγ from the culture. These components ordinarily will be of yeast, prokaryotic or non-human higher eukaryotic origin and preferably are present in innocuous contaminant quantities, on the order of less than about 1 percent by weight. Further, recombinant cell culture enables the production of IL-4bpγ free of proteins which may be normally associated with IL-4bpγ as it is found in nature in its species of origin, e.g. in cells, cell exudates or body fluids.

Administration of IL-4bpγ Compositions

The present invention provides methods of using therapeutic compositions comprising an effective amount of IL-4bpγ proteins and a suitable diluent and carrier, and methods for suppressing IL-4-dependent immune responses in humans comprising administering an effective amount of IL-4bpγ. Use in conjunction with other soluble cytokine receptors, e.g., IL-4 receptor, IL-1 receptor or TNF receptor, is also contemplated.

For therapeutic use, purified IL-4bpγ is administered to a patient, preferably a human, for treatment in a manner appropriate to the indication. Thus, for example, IL-4bpγ compositions administered to suppress immune function can be given by bolus injection, continuous infusion, sustained release from implants, or other suitable technique. Typically, an IL-4bpγ therapeutic agent will be administered in the form of a composition comprising purified protein in conjunction with physiologically acceptable carriers, excipients or diluents. Such carriers will be nontoxic to recipients at the dosages and concentrations employed. Ordinarily, the preparation of such compositions entails combining IL-4bpγ with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with conspecific serum albumin are exemplary appropriate diluents. Preferably, product is formulated as a lyophilizate using appropriate excipient solutions (e.g., sucrose) as diluents. Appropriate dosages can be determined in trials; generally, IL-4bpγ dosages of from about 1 ng/kg/day to about 10 mg/kg/day are expected to induce a biological effect. The amount and frequency of administration will depend, of course, on such factors as the nature and severity of the indication being treated, the desired response, the condition of the patient, and so forth.

IL-4bpγ is administered for the purpose of inhibiting IL-4-mediated immune responses in a human. For example, IL-4bpγ may be useful to inhibit Ig-E antibody formation in the treatment of IL-4-mediated IgE-induced immediate hypersensitivity reactions, such as allergic rhinitis (common hay fever), bronchial asthma, atopic dermatitis and gastrointestinal food allergy.

IL-4bpγ compositions may also be used to regulate IL-4-mediated T-cell functions. Although T-cell dependent functions were formerly thought to be mediated principally by IL-2, recent studies have shown that under some circumstances T-cell growth and proliferation can be mediated by growth factors such as IL-4. IL-4bpγ, for example, may be useful in suppressing or inhibiting T-cell dependent responses to alloantigen. A variety of diseases or conditions are caused by an immune response to alloantigen, including allograft rejection and graft-versus-host reaction. In alloantigen-induced immune responses, IL-4bpγ may suppress lymphoproliferation and inflammation which result upon activation of T-cells. IL-4bpγ may therefore be potentially effective in the clinical treatment of, for example, rejection of allografts (such as skin, kidney, heart, lung liver and pancreas transplants), and graft-versus-host reactions in patients who have received bone marrow transplants.

IL-4bpγ may also be useful in clinical treatment of autoimmune dysfunctions, such as rheumatoid arthritis, diabetes, which are dependent upon the activation of T-cells against antigens not recognized as being indigenous to the host.

Because of the primary role IL-2 plays in the proliferation and differentiation of T-cells, combination therapy using IL-4bpγ, IL-4 receptor and IL-2 receptors may be preferred in the treatment of T-cell dependent dysfunctions.

The following examples are offered by way of illustration, and not by way of limitation.

EXAMPLES

EXAMPLE 1

Purification of Human IL-4 Binding Protein-γ to Homogeneity

Human IL-4bpγ was isolated from human JM-1 cells (ATCC 10423) as follows. A human IL-4 affinity column was prepared by coupling 360 μg of recombinant human IL-4 to 1 ml AminoLink ™ gel (Pierce) according to the manufacturer's suggestions. IL-4 is dissolved in coupling buffer (0.1M phosphate, pH 7.0, 0.05% sodium azide in deoinized filtered (0.2μ) water) to a concentration of 1–20 mg/ml. A pre-packed 2 ml column containing 1 ml of cross-linked, 6%, beaded agarose gel was then equilibrated by applying 6 ml of the coupling buffer and followed by 2 ml of the protein solution (in coupling buffer). 0.2 ml of reducing solution (0.5 ml of 0.01N NaOH or distilled water, added to 32 mg of sodium cyanoborohydride). The gel is inverted several times and agitated gently by shaking for 2 hours at room temperature and allowed to stand for an additional 4 hours at 4° C. without mixing. The gel is washed with 4 ml of coupling buffer. The amount of protein that has been coupled can be determined by comparing the protein concentration of the original solution to that of the effluent by BCA (BCA Protein Assay, Pierce). The gel is equilibrated by addition of 4 ml of quenching buffer (1.0M Tris-HCl, pH 7.4) after which an additional 2 ml of quenching buffer, followed by addition of 0.2 ml of reducing solution. The gel is resuspended and the column mixed as described above for 30 minutes at room temperature. The gel is then washed with 20 ml of 0.5M NaCl/PBS, followed by 15 ml degassed 0.05% sodium azide in PBS.

JM-1 cells were grown to high density in RPMI-1640+10% FBS and then transferred to RPMI+1% FBS for 36 hours. The conditioned media from the JM-1 cells was then concentrated 200–400 fold on a Centriprep 10 ® 15 ml concentrator device (Amicon). The retentate was continually concentrated at 4° C. until a 200–400 fold concentration by volume was achieved. The resulting concentrate was stored in sterile polyproylene tubes at 4° C.

JM-1 concentrate (0.5–1.0 ml) was loaded onto the human IL-4 affinity column, prepared as described above. After 1 hr of incubation at room temperature unbound material (flow through) was collected and the column washed with 10 column volumes of PBS/0.5M NaCl to remove non-specifically bound protein. Proteins specifically binding to the IL-4 matrix were eluted from the column with 100 mM citrate buffer, pH 2.8. Eight to 10 500 ul fractions were collected and were immediately neutralized with 1.0M Hepes, pH 8.5. Protein in each fraction was estimated by $A_{280}$ using an extinction coefficient of 1.0. Protein was repeatedly detected in fractions 3,4 and 5 corresponding to 1.5 column volumes. These same fractions were pooled and concentrated using an Centricon-10 microconcentrator (Amicon) and protein estimated in the unpooled fractions and the IL-4 binding protein (IL-4bpγ) concentrate using the Pierce Bicinchoninic acid (BCA) protein assay reagent with bovine serum albumin as the standard. Samples of the IL-4pb concentrate were subjected to SDS-PAGE under reducing conditions on 8–25% and 10–15% gradient gels (Pharmacia) using molecular weight standards ranging from 12–95 kDa. Two major protein bands were detected by standard silver staining or coomasie blue staining methods, such as is described by Urdal et al., *Proc. Natl. Acad. Sci. USA* 81:6481 (1984).

Purification by the foregoing process permitted identification by silver staining or coomasie blue staining of polyacylamide gels of two separate major bands of 70 kDa and 45–50 kDa.

The two major bands were transferred from the SDS-PAGE gels to PVDF membrane, excised and sequenced as set forth in Example 2.

EXAMPLE 2

Sequencing of IL-4 Binding Protein

Amino terminal protein sequence of the two bands identified in Example 1 were obtained by excising bands from the gels and subjecting to automated Edman degradation on an Applied Biosystems Model 477A Protein Sequencer essentially as described by March et al. (*Nature* 315:641, 1985), except that PTH amino acids were automatically injected and analyzed on line with an Applied Biosystems Model 120A HPLC using a gradient and detection system supplied by the manufacturer. The 70 kDa band was determined to be bovine serum albumin. The smaller 45–50 kDa band was determined to be a novel IL-4 binding protein having the following amino terminal sequence, as determined from multiple sequencing runs:

ThrSerProGlnGlnProAlaAlaArgProSerAspLeuLeuSerLeuAspGlySer
1  2  3  4  5  6  7  8  9  10 11 12 13 14 15 16 17 18 19

This sequence of amino acids was used to search the NBRF old and new protein sequence data base. No identical proteins were found by this search. No similarity was noted with human or murine IL-4 receptor. The yield of IL-4bpγ from 400 ml of conditioned medium (concentrated to 1 ml) was calculated to be about 6–7 ug by BCA (Pierce). Human IL-4bpγ was then characterized functionally by the assays set forth in Examples 3 and 4.

Additional IL-4bpγ is purified by the method of Example 1 and sequenced as described above to obtain additional sequence information.

EXAMPLE 3

Inhibition of IL-4 Binding to IL-4 Receptors with IL-4bpγ

IL-4bpγ was shown to bind IL-4 by its ability to inhibit binding of IL-4 to various target cells which express IL-4 receptors. The target cells were stained with biotinylated human and murine IL-4, followed by streptavidin-phycoerythrin, and analyzed by flow cytometry, as follows.

In a first experiment, protein present in 100× concentrated supernatant of the human pre-B cell line JM-1 (derived as described by Park et al., *J. Bio. Chem.* 264:5420, 1989) was eluted from the IL-4 affinity column described in Example 1. The IL-4 affinity column eluate from from JM-1 supernatants (4.5 ug) was incubated for 1 hour at 4° C. with 250 ng of biotinylated human IL-4. All dilutions were made in PBS+0.02% NaN$_3$. Controls consisted of PBS alone in the place of column eluate. $5 \times 10^5$ target cells were then added and incubated 30 minutes at 4° C. In a second experiment, protein present in 200–400× concentrated supernatant of JM-1 cells was eluted from the IL-4 affinity column and incubated as described above with biotinylated human IL-4. JM-1 cells were added to JM-1 supernatant eluate/biotinIL-4 mixtures. After washing twice in PBS+NaN$_3$, the cells were incubated 30 minutes at 4° C. with 25 ul of 1:5 streptavidin-phycoerythrin (diluted in PBS+NaN$_3$). Following washing, the cells were analyzed by flow cytometry on a FACSCAN ® flow cytometer (Becton Dickinson) to determine intensity of biotinylated cytokine staining.

In additional experiments, using the same procedures described above, 15 µl of concentrated JM-1 supernatants (not purified on the IL-4 affinity column) were added to the biotinylated cytokines in lieu of the IL-4 column eluates, to which were added JM-1 cells.

These experiments show that IL-4bpγ (in the form of column purified protein and concentrated supernatants) binds to biotinylated human IL-4 and prevents the biotinylated IL-4 from binding to JM-1 and CTLL cells expressing human IL-4 receptor. IL-4bpγ, however, did not bid to biotinylated murine IL-4 and does not therefore inhibit binding of murine IL-4 to endogenous murine IL-4 receptors on the CTLL cell line.

Table A, below, shows the percent inhibition of biotinylated cytokine binding compared to staining with biotinylated cytokine alone.

TABLE A

| | % Inhibition of Biotinylated Cytokine Binding | | | |
|---|---|---|---|---|
| Target Cell Biotinylated Cytokine | JM-1 (exp #1) huIL-4 | JM-1 (exp #2) huIL-4 | CTLL huIL-4 | CTLL muIL-4 |
| Column eluate from JM-1 supernatants | 95 | 68 | 15 | 0 |
| Concentrated JM-1 supernatants | 100 | — | 15 | 0 |

This data indicates that human IL-4bp binds to IL-4 and inhibits binding of IL-4 to IL-4 receptors.

EXAMPLE 4

Inhibition of IL-4-Induced CTLL Cell Proliferation by IL-4bpγ

IL-4bpγ was shown to inhibit IL-4-dependent CTLL cell proliferation by the following assay. The murine T cell line CTLL-2 (ATCC TIB 214) was tansfected with IL-4 receptor DNA using conventional methods and designated CTLL-D. The CTLL-D cell line expresses human IL-4 receptor on the cell surface and responds to human IL-4 by proliferating. Inhibition of IL-4-dependent CTLL-D cell proliferation was determined by measuring radioactivity, which is a function of the number of new cells which incorporate [$^3$H]TdR for synthesis of new DNA.

CTLL-D cells were washed extensively and cultured in flat-bottom microtiter plates (4,000 cells/well) at 37° C. in 100 µl of DMEM, 10% FCS, in the presence of three-fold serial dilutions of IL-4bpγ (4 µg/ml, 1.3 µg/ml, 0.4 µg/ml and 0.13 µg/ml) and 150 pg/ml of human IL-4. The cells were pulsed with 1 µCi [$^3$H]TdR (Amersham Corp., Arlington Heights, Ill.) for the last 6 hours of a 24 hour incubation period. The cells were then harvested onto glass strips and [$^3$H]TdR incorporation was determined by measuring radioactivity on a Packard Tricarb 460 liquid scintillation counter. The results shown in FIG. 1 are triplicate, independent experiments.

These results show that increasing concentrations of IL-4bpβ and IL-4bpγ inhibit proliferation of CTLL-D cells, as determined by measuring radioactivity (cpm). These results are somewhat enigmatic in that the baseline (IL-4 added alone) is 36,586±7430 cpm, while the lowest concentration of IL-4bp (0.13 ug/ml) suddenly jumps to about 50,000 cpm. One would expect IL-4bp inhibition to result in a reduction of cpm below the IL-4 baseline. Nevertheless, the results clearly show a reduction of cpm with higher concentrations of IL-4bp, indicating that IL-4bpγ is an IL-4 antagonist in a biological system.

EXAMPLE 5

Purification of Recombinant IL-4bpγ

The following example illustrates methods for isolating recombinant forms of IL-4bpγ by cloning cDNA sequences encoding IL-4bpγ and isolating recombinant IL-4bpγ. Section A describes the construction of a cDNA library in λZAP. Section B describes a method for cloning IL-4bpγ DNA in which IL-4bpγ is cloned by screening the cDNA library with a probe generated by mixed oligonucleotide primer amplification of cDNA. Section C describes a method for cloning IL-4bpγ DNA in which degenerate oligonucleotide probes are used to screen Northern blots, a cDNA library or a genomic library. Section D describes the expression of IL-4bpγ cDNAs in COS cells.

A. Construction of a cDNA Library

A cDNA library in λZAP is constructed from polyadenylated mRNA isolated from the human cell line producing IL-4bpγ, such as JM-1 or other pre-B cell line (e.g., BMB or Nalm-6), using standard techniques, as described by Gubler et al., *Gene* 25:263, 1983, Ausubel et al., eds., *Current Protocols in Molecular Biology*, Vol. 1, 1987. Briefly, mRNA is reverse transcribed using oligo dT as primer, the resulting single stranded cDNA is rendered double stranded with DNA polymerase I, blunt-ended with T4 DNA polymerase, methylated with EcoRI methylase to protect EcoRI cleavage sites within the cDNA, and ligated to EcoRI linkers. The resulting constructs are digested with EcoRI to remove all but one copy of the linkers at each end of the cDNA, and ligated to an equimolar concentration of EcoRI cut and dephosphorylated λZAP ® arms obtained from Stratagene, San Diego, Calif., USA. The resulting ligation mix is packaged in vitro with the commercially available sonicated *E. coli* extract Gigapack ® (Stratagene, San Diego, Calif., USA) according to the manufacturer's instructions. Other suitable methods and reagents for generating cDNA libraries in a λ phage vectors are described by Huynh et al., *DNA Cloning Techniques: A Practical Approach*, IRL Press, Oxford (1984); Meissner et al., *Proc. Natl. Acad. Sci. USA* 84:4171 (1987), and Ausubel et al., supra λZAP ® is a phage λ cloning vector similar to λgt11 (U.S. Pat. No. 4,788,135) containing plasmid sequences from pUCl9 (Norrander et al., *Gene* 26:101, 1987), a polylinker site located in a lacZ gene fragment, and an f1 phage origin of replication permitting recovery of ssDNA when host bacteria are superinfected with f1 helper phage. DNA is excised in the form of a plasmid (comprising the foregoing elements) designated Bluescript ®. λZAP ®, Bluescript ®, and Gigapack ® are registered trademarks of Stratagene, San Diego, Calif., USA.

B. Screening of JM-1 cDNA Library with Specific cDNA Probes

Specific cDNA probes are derived by isolating total messenger RNA (mRNA) from JM-1 cells, which is then used to generate single strand cDNA (sscDNA). Mixed oligonucleotide primers complementary to reverse translation products of known IL-4bpγ amino acid sequences (obtained as described above in Example 2) are synthesized and the mixed oligonucleotide primers are then used to amplify the sscDNA sequences by polymerase chain reaction (PCR). The resulting amplification product is used as a probe to screen a cDNA library.

The specific cDNA probes are generated by the method of mixed oligonucleotide primed amplification of cDNA (MOPAC), substantially as described by Lee et al., *Science* 239:1288 (1988) and Innis et al., eds., *PCR Protocols: A Guide to Methods and Applications* (Academic Press, 1990). Total mRNA is first isolated from a cellular source of IL-4bpγ, such as the human cell line JM-1, using standard techniques, as described by Gubler et al., *Gene* 25:263, 1983, Ausubel et al., eds., *Current Protocols in Molecular Biology*, Vol 1, 1987.

In order to design and synthesize mixed oligonucleotide primers (sense primers and anti-sense primers) for use in PCR amplification it was first necessary to isolate sufficient quantities of IL-4bpγ to enable complete sequencing of an N-terminal region of IL-4bpγ. The location and length of the priming regions derived from the N-terminal amino acid sequence can be determined using the guidelines of Lee et al. (supra) and Innis et al., (supra). Briefly, each priming region is preferably from 15-20 base pairs in length and is located at least 18 base pairs from the other priming region. Suitable primer combinations are selected in accordance with the criteria of Lathe, *J. Mol. Biol.* 183:1 (1985). Degeneracy of the primers is restricted by selecting amino acids with minimal degeneracy and using only codons which are preferentially translated. The sequence of amino acids determined in Example 2 was used to synthesize degenerate primers corresponding to amino acids 1-6 (using only the non-degenerate nucleotides from amino acid 6) and amino acids 13-18 (using only the non-degenerate nucleotides from amino acid 18). Alternatively, the 5' primer corresponds to amino acids 3-7 (using only the non-degenerate nucleotides from amino acid 7). Due to the highly degenerate N-terminal amino acid sequence, the degenerate primers are broken down into separate pools for screening.

In the event that N-terminal amino acid sequence does not provide two priming regions meeting the criteria described by Lee et al. and Innis et al., additional amino acid sequence can be obtained in other regions of the IL-4bpγ by cyanogen bromide cleavage and sequencing. The sense and anti-sense primers are constructed with a suitable restriction enzyme linker on the 5' termini to facilitate rescue of the amplified cDNA into a cloning vector. In order to monitor the amplification of the cDNA, an internal (between the sense and antisense priming regions) oligonucloetide probe is synthesized.

The MOPAC protocol for obtaining a cDNA probe is performed substantially as described by Innis et al., eds. (supra) and Lee et al. (supra). Briefly, single strand cDNA (sscDNA) is generated from JM-1 total mRNA in a 50-ul reaction containing 50 mM Tris-HCl (pH 8.3), 75 mM KCl, 1 mM DDT, 15 mM MgCl2, 1 mM of each dNTP, 400 units of MuLV reverse transcriptase (Bethesda Research Labs, Inc., Bethesda, Md.), 5 μg of total RNA and 500 ng of oligto dT$_{(12-18)}$. The resulting cDNA mixture is then incubated at 37° C. for 1 hour, followed by heating to 95° C. for 5 min. to inactivate the MuLV reverse transcriptase.

The single-stranded DNA sample is amplified using the MOPAC procedure in a 100 ul reaction containing 10 mM Tris-HCl (pH 7.5), 50 mM NaCl, 10 mM MgCl2, 1 mM DTT, 1.5 mM of each dNTP, 1 μg of RNase A (DNase free), the sscDNA sample, and 3 μM of each prime mixture. After heating to 95° C. for 3 minutes, the reaction mixture is cooled to 37° C. for 15 minutes to allow the primers and cDNA to anneal. Five units of Klenow fragment (USB) is added and chain polymerization is carried out for 2 minutes at 37° C. The reaction mixture is denatured at 95° C. for 1 minute, annealed at 37° C. for 30 seconds, and 5 units of Klenow fragment added, followed by chain polymerization at 37° C. for 2 minutes. This is repeated for an additional 29 cycles.

Alternatively, the sscDNA sample is amplified with reagents obtained rom a GeneAmp DNA Amplification Kit with Taq polymerase (Perkin-Elmer Cetus) using 4 μM primer mixture and 30 cycles of PCR consisting of 95° C. for 1 minute, 37° C. for 30 seconds and 37° C. for 2 minutes for each cyle. The optimal temperature and timing of each cycle can be determined empirically utilizing the predicted EtBr staining pattern or Southern blots as the readout.

A 10 ul aliquot of the resulting reaction product is analyzed in a 4% NuSieve agarose gel followed by staining with EtBr to confirm that the DNA fragment size is consistent with the predicted product. The cDNA is then transferred by Southern Blotting to Zetabind membrane. The internal probe is end-labeled in the presence of $[\gamma^{32}P]dATP$ (3000 Ci/mmol) by T4polynucleotide kinase as described by Maniatis et al., *Molecular Cloning: A Laboratory Manual* (Cold Spring Harbor Laboratory, Cold Spring Harbor, N.Y., 1982). At appropriate hybridization temperature and conditions (determined empirically by standard procedures), the probe hybridizes to a product of the expected size in the amplified fraction, but not in the preamplified fraction.

The amplified cDNA is cloned by digesting with appropriate restriction enzymes, and subcloning into corresponding restriction sites of Bluescript, pGEM or other suitable cloning vector by standard procedures. The cloning vector is transformed into bacteria. Clones containing sequences complementary to the cDNA insert are identified by direct plasmid analysis of the transformed colonies or by in situ hybridization of the transformed colonies with the internal probe. A positive clone is sequenced by the dideoxy method.

The resulting clone is then used as a probe to isolate the full-length human IL-4bpγ cDNA from a JM-1 cDNA library (or used to screen previously constructed human cDNA libraries) as follows. The library is plated on bacterial cells and incubated overnight at 37° C. Duplicate plaque lift filters are incubated with the cDNA probe in hybridization buffer under conditions of high stringency. Filters are then washed. Positive plaques hybridizing to the probe are picked. Bluescript ® plasmids containing the cDNA inserts are excised from the phage and transformed into *E. coli*. Plasmid DNA is isolated from individual colonies, and analyzed by restriction enxzyme digestion and Southern blot analysis by standard methods. All manipulations of λZAP ® and excision of the Bluescript ® plasmid are as described by Short et al., (*Nucl. Acids Res.* 16:7583, 1988) and Stratagene product literature. This procedure results in the isolation of a cDNA clone coding for human IL-4bpγ from the cDNA library generated from the JM-1 cell line.

Bluescript ® plasmids containing the cDNA inserts are excised from the phage as described by the manufacturer and transformed into *E. coli*. Plasmid DNA is isolated from individual colonies, digested with an appropriate restriction enzyme to release the cDNA inserts and electrophoresed on standard 1% agarose gels.

Duplicate gels are blotted onto nylon filters to produce identical Southern blots for analysis with various probes (such as from other regions of the DNA sequence) and the cDNA clone is sequenced by standard methods.

C. Screening of Recombinant cDNA Clones with Synthetic Oligonucleotide Probes

Recombinant cDNA clones encoding IL-4bpγ can also be isolated by the conventional method of screening Northern blots with a mixture of synthetic degenerate oligonucleotide probes. Partial N-terminal amino acid sequence of IL-4bpγ is used to design sets of oligonucleotide 20-mers, which are complementary to various possible nucleotide sequences encoding the amino acid sequence. The 5' end of these mixed synthetic oligonucleotides are $^{32}$P-labeled using T4 polynucleotide kinase and [γ-$^{32}$P]ATP and used to probe replicate Northern blots containing RNA prepared from the JM-1 cells and replicate Northern blots containing RNA from a cell line that does not produce IL-4bpγ (negative control). Briefly, RNA is fractionated for Northern blot by agarose slab gel electrophoresis under fully denaturing conditions using 10 mM methyl mercury (CH$_3$HgOH) as the denaturant as described by Bailey, et al. *Anal. Biochem.* 70:75, 1976; and Sehgal, et al., *Nature* 288:95, 1980. 1.5% gels are prepared by melting agarose in running buffer (100 mM boric acid, 6 mM sodium borate, 10 mM sodium sulfate, 1 mM EDTA, pH 8.2), cooling to 60° C. and adding 1/100 volume of a M CH3HgOH. The RNA is dissolved in 0.5× running buffer and denatured by incubation 10 mM methyl mercury for 10 minutes at room temperature. Glycerol (20%) and bromophenol blue (0.05%) are added for loading the samples. Samples are electrophoresed for 500–600 volt-hr with recirculation of the buffer. After electrophoresis, the gel is washed for 40 minutes in 10 mM 2-mercaptoethanol to detoxify the methyl mercury, and Northern blots prepared by transferring the RNA from the gel to a membrane filter.

Similar gels are prepared by identical extraction and purification of mRNA from different cells which are known not to produce IL-4bpγ. These samples are used as controls for hybridization with probe mixtures.

The gels for Northern blot are prehybridized at 25°–42° C. for 6–8 hours with 10 ml per filter of hybridization buffer (6× SSC, pH 7.0, 5× Denhardt's solution, 50 mM sodium phosphate buffer at pH 7.0, 0.2% SDS, and 50 ug/ml denatured salmon sperm DNA) without the probe. Each set of oligonucleotides is hybridized to the membrane filter at a series of temperatures between 42° C. and 60° C. in hybridization buffer and washed in 6× SSC, 0.1% SDS at the hybridization temperature. A particular set of oligonucleotides and a particular hybridization temperature giving a signal from JM-1 cells and not from the negative control is selected.

The selected set of oligonucleotides is then used to screen a JM-1 cDNA library in λZAP or λgt10 (using standard techniques) to isolate a complete or larger partial coding sequence for human IL-4bpγ. Larger partial coding sequences are used to rescreen the library for complete sequences. Hybridization conditions for screening the library with the selected set of oligos are at a temperature bout 5° C. lower than that determined from Northern hybridization. Washing conditions are at the hybridization temperature in 6× SSC, 0.1% SDS. Excessive background may be reduced by using lower salt or higher temperature conditions, which are determined empirically.

Positive clones are reprobed with other oligos derived from alternate regions of the sequence, or directly directly sequenced to verify their identity.

As an alternative to probing mRNA by Northern blot, an IL-4bp clone can be isolated by screening bacteriophage cDNA or genomic libraries with degenerate oligos using the colony hybridization procedure. In this method, the cDNA or genomic library is plated on bacterial cells and incubated overnight at 37° C. until bacteriophage plaques cover the plate but are not confluent. Duplicate nitrocellulose filters are applied face down on each of the plates bearing the bacteriophage plaques in order to allow the phage particles and unpackaged DNA to adsorb to the filter and produce a replica of the plate surface. The filters are treated with 0.2M NaOH/1.5M NaCl to destroy the phage particles and denature the phage DNA which then binds to the nictrocellulose. The filters are then neutralized with 0.4M Tris-Cl, pH 7.6 and 2× SSC for 1–2 minutes, after which the filters are air dried and baked at 80° C. for 2 hours.

The duplicate filters for cDNA or genomic screening are prehybridized at 25°–42° C. for 6–8 hours with 10 ml per filter of hybridization buffer (6× SSC, pH 7.0, 5× Denhardt's solution, 50 mM sodium phosphate buffer at pH 7.0, 0.2% SDS, and 50 ug/ml denatured salmon sperm DNA) without the probe. The samples are then hybridized by incubation at the appropriate temperature for about 24–36 hours using the hybridization buffer containing the kinased probe.

Hybridization of these filters to a DNA or RNA probe identifies the location of the phage plaque containing IL-4bpγ cDNA, which is then recovered from the plate.

D. Expression of Human IL-4bpγ

IL-4bpγ clones which are verified to be full-length (by sequencing) are excised from the cloning vector using a suitable restriction enzyme (or enzymes) that does not cut within the insert and inserted into an expression vector, such as pDC302 (described by Mosley, et al., *Cell* 59:335, 1989).

The pDC302/IL-4bpγ plasmid is then transferred into COS cells using DEAE-dextran followed by chloroquine treatment, as described by Luthman et al, *Nucl. Acids Res.* 11:1295, 1983 and McCutchan et al., *J. Natl. Cancer Inst.* 41:351, 1968. The cells are then grown in culture for three days and the cell supernatants are assayed for IL-4bpγ activity as described in Example 3 to confirm IL-4 binding activity.

EXAMPLE 6

Preparation of Monoclonal Antibodies to IL-4bpγ

Preparations of purified recombinant IL-4bpγ or transfected COS cells expressing high levels of IL-4bpγ, JM-1 or NALM6 cells, or synthetic peptides derived from the amino terminal amino acid sequence are used as an immunogen to generate monoclonal antibodies against IL-4bpγ using conventional techniques, such as those disclosed in U.S. Pat. No. 4,411,993. Such antibodies are likely to be useful in interfering with IL-4 binding to IL-4 receptors, for example, in ameliorating toxic or other undesired effects of IL-4.

To immunize rats, an IL-4bpγ peptide comprising the first 12 amino acids of the IL-4bpg sequence coupled to ovalbumin were used as immunogen emulsified in complete Freund's adjuvant and injected in amounts ranging from 10–200 µl subcutaneously into Lewis rats.

Three weeks later, the immunized animals are boosted with additional immunogen emulsified in incomplete Freund's adjuvant and boosted every three weeks thereafter. Serum samples are periodically taken by retro-orbital bleeding or tail-tip excision for testing by dot-blot assay, ELISA (enzyme-linked immunosorbent assay), or inhibition of binding of $^{125}$I-IL-4 to extracts of IL-4bpγ bearing cells. Other assay procedures are also suitable. Following detection of an appropriate antibody titer, positive animals are given a final intravenous injection of antigen in saline. Three to four days later, the animals are sacrificed, splenocytes harvested, and fused to the murine myeloma cell line AG8653. Hybridoma cell lines generated by this procedure are plated in multiple microtiter plates in a HAT selective medium (hypoxanthine, aminopterin, and thymidine) to inhibit proliferation of non-fused cells, myeloma hybrids, and spleen cell hybrids.

Hybridoma clones thus generated are screened for reactivity with IL-4bpγ. Initial screening of hybridoma supernatants utilize an antibody capture and binding of partially purified $^{125}$I-IL-4bpγ. Positive hybridomas screened by this method are tested by a modified antibody capture to detect blocking antibody. Positive antibodies are capable of immunoprecipitating human IL-4bpγ protein from JM-1 cells or COS-7 cells transfected with IL-4bpγ clones labelled with $^{35}$S-cysteine/methionine. The anti-IL-4bpγ hybridomas are then injected into the peritoneal cavities of nude mice to produce ascites containing high concentrations (>1 mg/ml) of anti-IL-4bpγ monoclonal antibody. The resulting monoclonal antibody was purified by ammonium sulfate precipitation followed by gel exclusion chromatography, and/or affinity chromatography based on binding of antibody to Protein G.

---

---

We claim:

1. An isolated and purified Interleukin-4 Binding Protein-γ comprising an N-terminal amino acid sequence of ThrSerProGlnGlnProAlaAlaArgProSerAspLeuLeuSerLeuAspGlySer (SEQ ID NO:1), that is capable of binding to Interleukin-4 and inhibiting binding of Interleukin-4 to a cell surface receptor, wherein the Interleukin-4 Binding Protein-γ is of human origin.

2. An isolated and purified Interleukin-4 Binding Protein-γ according to claim 1, comprising Interleukin-4 Binding Protein-γ in the form of a glycoprotein.

3. An isolated and purified Interleukin-4 Binding Protein-γ according to claim 2, wherein the Interleukin-4 Binding Protein-γ has an apparent molecular weight by SDS-PAGE of about 45-50 kilodaltons (kDa).

4. An isolated and purified Interleukin-4 Binding Protein-γ according to claim 2, wherein the Interleukin-4 Binding Protein-γ is derived from JM-1 cells.

* * * * *

UNITED STATES PATENT AND TRADEMARK OFFICE
CERTIFICATE OF CORRECTION

PATENT NO. : 5,223,605

DATED : June 29, 1993

INVENTOR(S) : William C. Fanslow and Richard J. Armitage

Page 1 of 2

It is certified that error appears in the above-identified patent and that said Letters Patent is hereby corrected as shown below:

Column 1, line 35, "Mosely" should be --Mosley--.
 line 68, "SDA" should be --SDS--.
Column 4, line 6, "in" should be --is--.
Column 5, line 8, "paring" should be --pairing--.
Column 7, line 28, "to" should be --or--.
 line 50, "nuecloetides" should be --nucleotides--.
Column 8, line 8, "of" should be --on--.
Column 9, line 37, "Russel" should be --Russell--.
Column 12, line 42, after "lung" please add --,--.
Column 13, line 2, "deoinized" should be --deionized--.
 line 33, "polyproylene" should be --polypropylene--.
 line 42, "ul" should be --µl--.
Column 14, line 31, "ug" should be --µg--.
 line 52, delete second "from" and correct "ug" to read --µg--.
 line 62, "eluate/biotinIL-4" should be --eluate/biotin-IL-4--.
 line 64, "ul" should be --µl--.
Column 15, line 14, "bid" should be --bind--.
 line 65, "ug/ml" should be --µg/ml--.
Column 16, line 47, the symbol for "registered trademark" should be superscript.
Column 17, line 56, "50-ul" should be --50-µl--.
 line 57, "DDT" should be --DTT-- and "MgC12" should be --MgCl$_2$--.
 line 65, "ul" should be --µl--.
 line 66, "MgC12" should be --MgCl$_2$--.
Column 18, line 1, "prime" should be --primer--.
 line 11, "rom" should be --from--.
 line 19, "ul" should be --µl--.
 line 55, "enxzyme" should be -- enzyme--.

UNITED STATES PATENT AND TRADEMARK OFFICE
CERTIFICATE OF CORRECTION

PATENT NO. : 5,223,605

DATED : June 29, 1993

INVENTOR(S) : William C. Fanslow and Richard J. Armitage

It is certified that error appears in the above-identified patent and that said Letters Patent is hereby corrected as shown below:

Column 19, line 31, after "incubation" and before "10" please add --in--.
           line 48, "ug/ml" should be --μg/ml--.
           line 63, "bout" should be --about--.
Column 20, line 2, please delete "directly".
           line 18, "nictrocellulose" should be --nitrocellulose--.
           line 26, "ug/ml" should be --μg/ml--.
         line 65, "IL-4bpg" should be --IL-4bpy--.

Signed and Sealed this

Sixth Day of September, 1994

Attest:

BRUCE LEHMAN

*Attesting Officer*      *Commissioner of Patents and Trademarks*